United States Patent [19]

Melker et al.

[11] Patent Number: 5,322,165
[45] Date of Patent: Jun. 21, 1994

[54] SHARP INSTRUMENT ENCASEMENT SYSTEM

[75] Inventors: Richard J. Melker; Gary J. Miller; Christopher D. Batich, all of Gainesville, Fla.

[73] Assignee: University of Florida, Gainesville, Fla.

[21] Appl. No.: 17,578

[22] Filed: Feb. 16, 1993

[51] Int. Cl.$^5$ ............................................. A61M 5/32
[52] U.S. Cl. ................................. 206/366; 206/365; 206/524.4; 604/110
[58] Field of Search .............. 206/365, 366, 367, 219, 206/524.4, 222, 820; 220/909, 910; 604/110

[56] References Cited

U.S. PATENT DOCUMENTS

| | | |
|---|---|---|
| 2,559,231 | 7/1951 | Seemar . |
| 2,568,029 | 9/1951 | Seemar . |
| 2,766,755 | 10/1956 | Greene . |
| 3,425,598 | 2/1969 | Kobernick . |
| 3,715,189 | 2/1973 | Nighohossian et al. ............ 206/222 |
| 3,715,856 | 2/1973 | Borel ................................... 206/820 |
| 4,103,771 | 8/1978 | Klatt et al. .......................... 206/219 |
| 4,279,340 | 7/1981 | Lang .................................... 206/219 |
| 4,728,321 | 3/1988 | Chen ................................... 604/110 |
| 4,808,006 | 2/1989 | Kaufeler .............................. 206/219 |
| 4,816,307 | 3/1989 | Honeycutt .......................... 206/366 |
| 4,845,923 | 7/1989 | Donovan ............................. 53/431 |
| 4,848,569 | 7/1989 | Leishman ........................... 206/365 |
| 4,900,500 | 2/1990 | Honeycutt .......................... 206/366 |
| 4,919,264 | 4/1990 | Shinall ................................. 206/366 |
| 4,919,569 | 4/1990 | Wittenzelliner . |
| 4,936,449 | 6/1990 | Conard et al. ...................... 206/366 |
| 4,950,242 | 8/1990 | Alvarez ............................... 604/110 |
| 4,973,315 | 11/1990 | Sincock ................................ 206/365 |
| 4,986,432 | 1/1991 | Anghileri ............................ 206/820 |
| 4,992,217 | 2/1991 | Spinello . |
| 5,038,929 | 8/1991 | Kubofcik ............................ 206/365 |
| 5,084,027 | 1/1992 | Bernard ............................... 604/192 |
| 5,104,704 | 4/1992 | Labes et al. . |
| 5,201,418 | 4/1993 | Hanlon ................................ 206/366 |

Primary Examiner—Paul T. Sewell
Assistant Examiner—Marie Denise Patterson
Attorney, Agent, or Firm—Salinwanchik & Salinwanchik

[57] ABSTRACT

A sharp instrument encasement system is disclosed for encasing the sharp points or edges of medical instruments. The system comprises a container having two fluid-tight compartments separated by a frangible membrane, one compartment containing a hardenable resin and the other containing a filler comprising a particulate material that is substantially incompressible. Upon insertion of a medical instrument through a penetrable top and through the frangible membrane, the contents of the compartments mix, creating a reaction that hardens the resin and particulate material mixture and encases the sharp portions of the medical instrument.

16 Claims, 2 Drawing Sheets

SHARP INSTRUMENT ENCASEMENT SYSTEM

TECHNICAL FIELD

The present invention relates to the safe disposal of medical instruments having sharp edges or points that may be contaminated by various infectious diseases. More particularly, the invention relates to an apparatus and method for rapid encasement of the sharp portions of medical instruments such as hypodermic needles, suturing needles, lancets, trocars, and scalpel blades, within a hard substance which permits quick disposal at the point of use of the medical instruments.

BACKGROUND OF THE INVENTION

The safe disposal of sharp, contaminated medical instruments is a major health care problem. Numerous infectious diseases can be transmitted to other persons through contact with the contaminated instruments during the disposal process. Hypodermic needles, trocars and other instruments that retain body tissue and fluids therein are particularly dangerous and are known to transmit such diseases as the AIDS virus, hepatitis, syphilis and tuberculosis. Disposing of the used medical instruments within the operating rooms, patient rooms and laboratories is a task that exposes the doctors, nurses and other hospital employees and visitors to inadvertent injuries and exposure to disease. Injuries frequently have occurred while trying to cap hypodermic needles in preparation for their transport and disposal through incineration or other means. Current procedures require the collection and removal of the dangerous "sharps" to another site for decontamination, encapsulation or other protective measures. This means that the unprotected medical instruments remain on the "hospital floors" while awaiting collection and transport permitting unauthorized retrieval of such equipment for improper uses. The greater the handling of the unprotected "sharps", the greater the opportunity for injury and infection.

Two patents issued to Honeycutt, U.S. Pat. Nos. 4,816,307 and 4,900,500 and a patent issued to Donovan, U.S. Pat. No. 4,845,923 each disclose methods for encasing "sharps" in containers containing resins which harden and encapsulate the instruments. The processes identified in these patents are still slow reacting, do not provide a capsule that is resistent to crushing and in some cases require handling of chemicals by the staff at the point of use. It is clear that a device that accepts the instruments immediately after use and quickly encases the sharp portions of the instruments upon the simple insertion of the instrument into an individual container is needed.

SUMMARY OF THE INVENTION

Briefly, this invention comprises a container which is sized to receive at least the sharp portion of at least one instrument. The container has a flexible top that is penetrable by the sharp instrument and further comprises two fluid-tight compartments that are disposed one above the other with a frangible membrane therebetween. A filler that is comprised of a substantially incompressible particulate material is in one of the compartments and a hardenable resin is placed in the other compartment. Upon insertion of the medical instrument through the penetrable top and into the container, the frangible membrane is shattered permitting the contents of each of the compartments to mix with one another so that the resin and the filler adhere to and harden about the sharp portions of the medical instrument.

BRIEF DESCRIPTION OF THE DRAWING

Particularly preferred embodiments of the apparatus of this invention will be disclosed in detail in which.

Similar reference characters refer to similar parts throughout the several views of the

DETAILED DESCRIPTION

Figure 1:
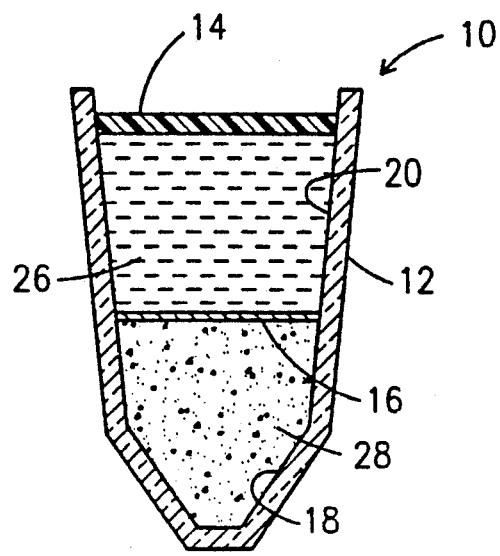
FIG. 1 is a cross-sectional view of one embodiment of the invention, illustrating the filler in the bottom compartment and the liquid resin in the top compartment.
Figure 2:
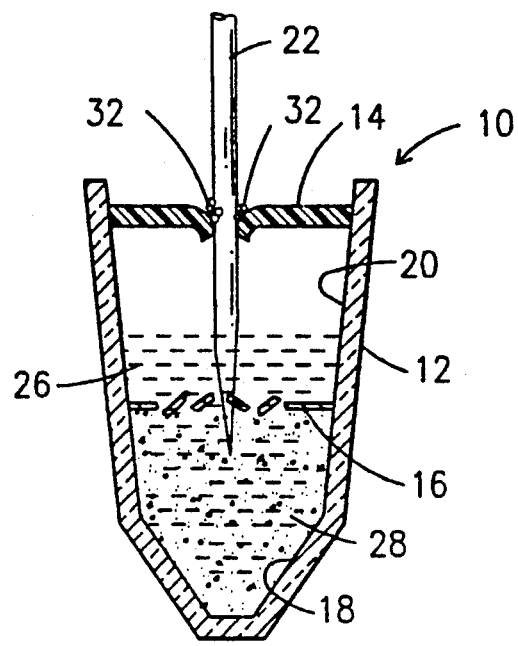
FIG. 2 is a cross-sectional view of the invention as shown in FIG. 1 illustrating the insertion of a needle into the encasement unit.
Figure 3:
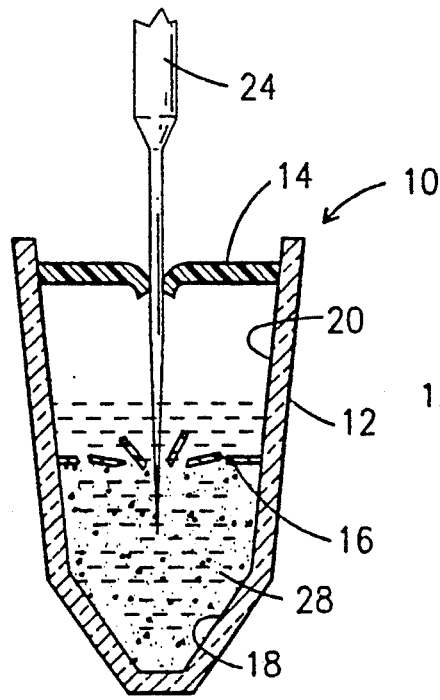
FIG. 3 is a cross-sectional view of the invention of FIG. 1, illustrating the insertion of a scalpel into the encasement unit.
Figure 4:
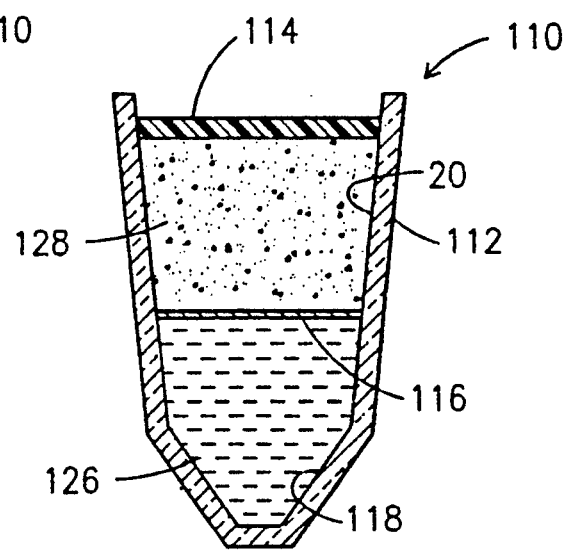
FIG. 4 is a cross-sectional view of a second embodiment of the invention, illustrating the liquid resin in the lower compartment and the filler in the upper compartment.

A preferred embodiment of the sharp instrument encasement system is illustrated in FIGS. 1–3 in which the apparatus, or encasement unit, is generally indicated as 10. FIG. 4 illustrates a second embodiment, which is indicated as 110, and all other reference characters for this embodiment correspond to those for FIGS. 1–3, incremented by 100. The apparatus is used to protect persons who are exposed to used and contaminated sharp medical devices that include, but are not limited to, hypodermic needles, trocars, and any other medical device with a sharp tip or edge that is connected to a hollow body that can house a bacteria or virus. Also, scalpels, lancets, and other medical instruments that have a sharp tip or edge may be disposed of in the same or similar apparatus.

Figure 5:
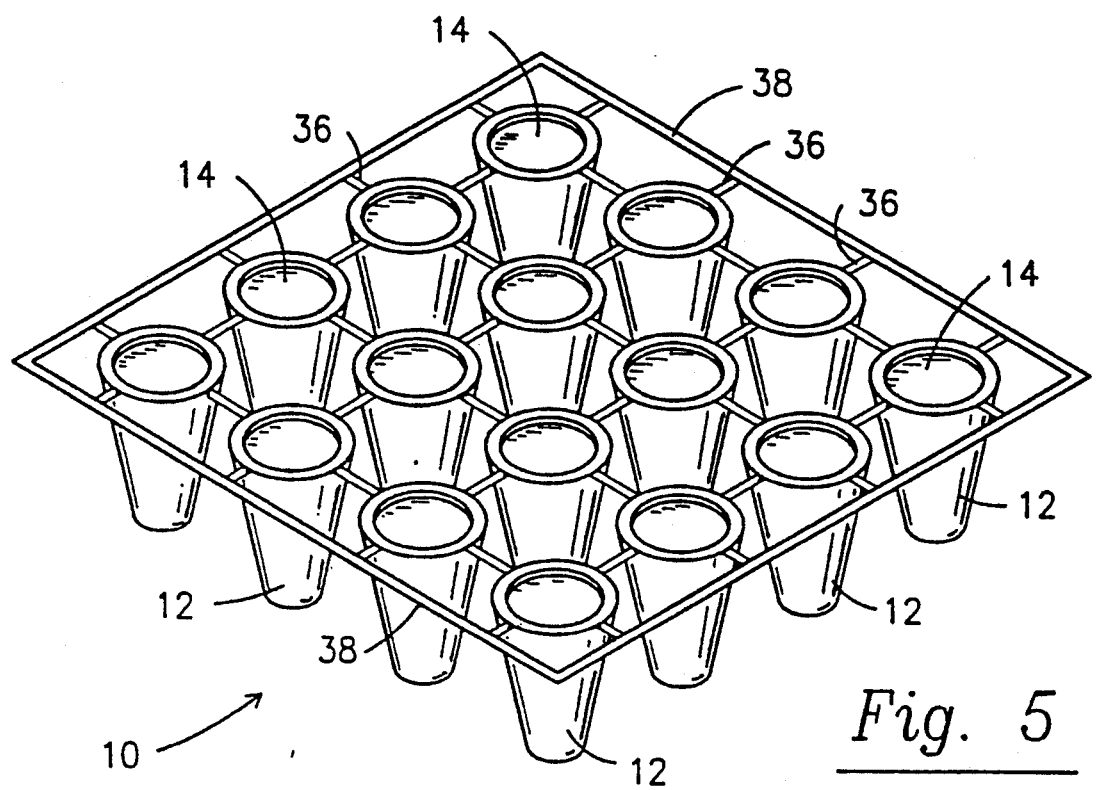
FIG. 5 is a perspective view of a plurality of the encasement units of this invention formed into a grid.
Figure 6:
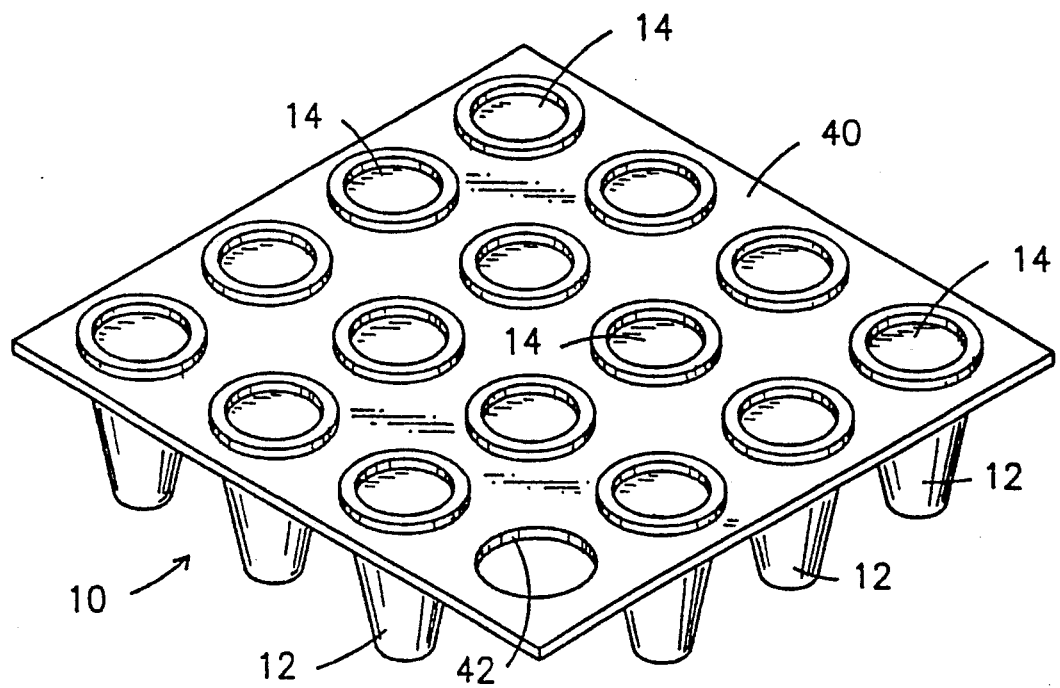
FIG. 6 is a perspective view of a plurality of the encasement units carried by a tray.

As seen in FIG. 1, the apparatus 10 comprises a container 12 suitably formed of a generally rigid synthetic resin and preferably one that is transparent or translucent, which container has a penetrable top 14 formed of a resilient, rubber-like synthetic resin and a frangible membrane 16, which divides the container into two fluid-tight compartments, a lower compartment 18 and an upper compartment 20. The container 12 may be made to any suitable size to accept the sharp portions of most sharp medical instruments. In this particular preferred embodiment only the sharp portions of the instrument are received within the container 12; however, larger containers could be made to accept the whole medical instrument if it were deemed desirable. The encasement of the sharp portions of a hypodermic needle 22 is illustrated in FIG. 5, with a corresponding unit for a scalpel 24 illustrated in FIG. 6.

One compartment of the apparatus contains a hardenable resin 26, preferably a cyanoacrylate ester, and the other compartment contains a filler 28 that is comprised of a particulate material having a high modulus of a hardness, such as a fine grain silica sand, which is substantially incompressible. In the preferred embodiment a methyl cyanoacrylate is preferred over ethyl or purple cyanoacrylate, although the two latter materials can be used if desired. The viscosity of the resin may be easily adjusted, but a consistency generally similar to that of water is generally preferred to ensure rapid penetration of the voids between the grains in the filler 28 when the two components are combined. The grain size of particulate matter of the filler 28 may be sized to be received within the apertures of any of the medical instruments that are to be disposed of with this apparatus, particularly hypodermic needles. By filling the needle with resin and filler a better bond will be obtained. There should be enough filler 28 within the container 12 to ensure covering the sharp portions of the instrument, and there should be enough resin 26 to fill the voids of the filler 28.

In the preferred embodiment an accelerator is used to speed up the hardening of the resin 26 and filler 28 mixture. The length of time that it takes for the resin 26 to harden is important. If the reaction is too slow, it becomes a safety problem, as the instruments may be removed from the container before the resin has hardened about the instrument's sharp edges. If the reaction is too fast, the resin will harden before it has substantially penetrated the voids of the filler 28, preventing a complete seal about the medical instrument. The type of resin and amount of any accelerator to be used generally determines the speed of reaction. In the preferred embodiment the accelerator is a strong base, such as sodium bicarbonate, which is mixed with the filler 28 in the proportions necessary for optimal hardening. Approximately a one to one ratio of sodium bicarbonate to sand by volume will provide a reaction time of two to three seconds, which is considered desirable. In other embodiments para-toluidine may be used as an accelerator, and it may be applied to the particles of the filler as a coating for even distribution of the accelerator.

In one embodiment, to ensure complete mixing of the resin 26 with the sand filler 28, a pressure differential is established between the compartments, the compartment holding the filler 28 having a lower pressure than the compartment holding the resin 26. For example, as mentioned previously, in one embodiment the sand and sodium bicarbonate mixture is placed in the lower compartment 18, and the resin is placed in the upper compartment 20. When the frangible membrane 16 is breached by the instrument 22, as shown in FIG. 2, the liquid resin 26 is rapidly drawn by the lower pressure into the lower compartment 28, meeting less than normal resistance from trapped air, as the voids have been at least partially evacuated. In other embodiments, where there is no pressure differential between the compartments, gravity is relied upon to cause the liquid resin 26 to flow into the filler 28. In the embodiment illustrated in FIG. 4, the filler 28 is placed in the upper compartment 120 so that, when the frangible membrane 116 is broken, the sand/sodium bicarbonate filler mixture falls into the lower compartment 118 by gravity, mixing with the resin 26.

The frangible membrane 16 is preferably made from thin glass; however, a frangible plastic with similar properties may work as well. The glass or plastic membrane 16 may be etched to provide increased frangibility. It is desirable that the membrane 16 shatter rather than puncture so that the materials will pass through the breach in the membrane 16 quickly.

The penetrable top 14 is made of a flexible material such as rubber or other flexible synthetic resin that is well known and suitable for this purpose. Upon insertion of the instrument through the flexible top 20, the flexible material of the top 20 clings to the sides of the medical device, wiping off most of the attached tissue or other material 32 as shown in FIG. 2. This will both reduce contamination and improve bonding by the resin 26 to the instrument.

For ease of handling a plurality of the containers 12 may be joined to one another by frangible connectors 36, as shown in FIG. 5, to form a grid 38. The individual containers 12 may be removed from the grid 38 by breaking the adjacent connectors 36. The containers 12 may alternatively, be joined to one another by inserting them into a tray 40 having a plurality of holes 42 therethrough. The holes are sized and configured to receive a container 12 in each hole. Individual containers 12 may be removed for disposal or held by the tray 40 until all are used. The grids 38 and the trays 40 may be fabricated as squares, rectangles, strips or in any other suitable configuration.

With the apparatus of this invention described above, a typical mode of operation of one embodiment may now be described. For such operation the apparatus of the sharp instrument encasement system may conveniently be placed on the carts or at the work stations of the nurses and doctors where the instruments are being used. For example, after a nurse gives an injection, the hypodermic needle 22 is inserted immediately, point first, into a container 12, so that the needle shatters the frangible membrane 16 and penetrates into the filler 28. As the needle is inserted into the container, much of the tissue, fat cells or other materials 32 clinging to the outside are wiped from the exterior of the needle by the penetrable top 14 as shown in FIG. 2. As the needle is inserted into the container, resin may flow into the needle to react with the granules of filler with accelerator that are forced into the needle aperture as the needle penetrates the filler. This will then cause the point to be blocked by the hardened resin. When the membrane 16 is shattered by the needle 22, the lower pressure in the compartment holding the filler rapidly draws the resin into the voids of the filler. The resin reacts with the accelerator, becoming hard within a few seconds, suitably two or three seconds. The reaction of the resin 26 with the accelerator creates a toxic, exothermic reaction that kills most bacteria and viruses that are present. A coloring agent, of a type well known in the art, may be added to the filler so that the filler changes color upon completion of the hardening of the resin, signifying that the encapsulated medical instrument is now safe for disposal.

While the foregoing has described a particularly preferred embodiment and several additional embodiments of the sharp instrument encasement system, it is to be understood that this description is illustrative only of the principles of the invention and is not to be considered limitative thereof. Because of numerous modifications and variations of the disclosed apparatus, all within the scope of the invention, will readily occur to those skilled in the art, the scope of this invention is to be limited solely by the claims appended hereto.

What is claimed is:

1. An apparatus for the containment of sharp medical instruments comprising:
   a container sized to receive at least the sharp portion of at least one such instrument, said container having a top penetrable by the instrument, and a plurality of fluid-tight compartments disposed one above another with a frangible membrane therebetween;

a filler comprising a particulate material in one of said compartments; and a hardenable resin in another of said compartments, wherein the pressure within said compartment having said filler therein is less than the pressure in said other compartment containing said resin, whereby upon inserting the instrument into said container the instrument shatters said membrane permitting the contents of each said compartment to mix so that said resin and filler mixture hardens, encasing the sharp portion of the instrument.

2. An apparatus for the containment of sharp medical instruments comprising:

a container sized to receive at least the sharp portion of at least one said instrument, said container having a top penetrable by said instrument, and two fluid-tight compartments disposed one above the other with a frangible membrane therebetween;

a hardenable resin in one said compartment; and a filler in said other compartment, said compartment having a pressure therein less than the pressure in said compartment having said resin therein, such that upon inserting said instrument into said container sufficiently that said instrument shatters said membrane permitting the contents of each said compartment to mix, said resin and filler mixture hardens, whereby the sharp portion of said instrument are encased in hardened resin and filler material.

3. An apparatus as in claim 2 wherein said filler comprises a particulate material.

4. An apparatus as in claim 3 wherein said filler further comprises an accelerator mixed with said particulate material to accelerate the hardening of said resin when said resin contacts said accelerator.

5. An apparatus as in claim 4 wherein said accelerator comprises a base.

6. An apparatus as in claim 4 wherein said accelerator comprises sodium bicarbonate.

7. An apparatus as in claim 3 wherein said filler comprises an accelerator coating at least some of said particulate matter.

8. An apparatus as in claim 7 wherein said accelerator comprise para-toluidine.

9. An apparatus as in claim 2 wherein, when the sharp medical instrument to be subjected to containment has an aperture in the sharp portion thereof, said filler comprises particles being sufficiently small so as to be received within the aperture.

10. An apparatus as in claim 2 wherein said membrane comprises glass.

11. An apparatus as in claim 2 wherein said top of said container is flexible, such that said top remains in contact with said instrument while said instrument is inserted through said top into said container.

12. An apparatus as in claim 2 wherein said apparatus further comprises a tray having a plurality of openings therein each sized to receive one said container, whereby a plurality of said containers may be moved as a unit from place to place.

13. An apparatus as in claim 2 wherein said apparatus further comprises a plurality of containers and a plurality of frangible connectors joining adjacent said containers to one another to form a grid of said containers, whereby individual containers may be removed from said grid by breaking the connectors adjacent thereto.

14. An apparatus as in claim 2 wherein one said compartment has a coloring agent therein, said coloring agent changing color when said resin and said filler are mixed and said resin hardens.

15. An apparatus as in claim 2 wherein said resin is comprised of a cyanoacrylate ester.

16. A method for encasing a sharp medical instrument having an exterior surface, said exterior surface having material clinging thereto, said method comprising the steps of:

inserting said instrument into a container sized to receive at least the sharp portion of at least one said instrument through a sealed flexible top that engages said instrument during said insertion such that said material is substantially removed from said exterior surface of said instrument;

fracturing a frangible membrane with said instrument, said membrane separating a first fluid-tight compartment, containing a hardenable resin, from a second fluid-tight compartment disposed below said first compartment, said second compartment containing a filler comprising a particulate material, said particulate material being mixed with an accelerator, said second compartment being maintained at a pressure lower than the pressure within said first compartment, such that said hardenable resin is drawn into the voids of said mixture of particulate material and accelerator by said lower pressure, said hardenable resin reacting with said accelerator; and maintaining said medical instrument in said container until said mixture of hardenable resin, filler and accelerator has bonded to said instrument and hardened.

* * * * *

UNITED STATES PATENT AND TRADEMARK OFFICE
CERTIFICATE OF CORRECTION

PATENT NO.    :    5,322,165

DATED         :    June 21, 1994

INVENTOR(S)   :    Melker *et al.*

It is certified that error appears in the above-identified patent and that said Letters Patent is hereby corrected as shown below:

Column 5, line 46: Delete "comprise" and insert --comprises--.

Column 2, line 26: After "several views of the" insert --drawings--.

Signed and Sealed this

Twentieth Day of September, 1994

Attest:

BRUCE LEHMAN

Attesting Officer     Commissioner of Patents and Trademarks